United States Patent [19]
Jonsson

[11] Patent Number: 5,899,874
[45] Date of Patent: May 4, 1999

[54] PREPARATION AND METHOD FOR PRODUCTION OF PLATELET CONCENTRATES WITH SIGNIFICANTLY PROLONGED VIABILTY DURING STORAGE

[75] Inventor: Svante Jonsson, Glumslöv, Sweden

[73] Assignee: Stiftelsen for Medicinsk-Teknisk Utveckling, Sweden

[21] Appl. No.: 08/884,358

[22] Filed: Jun. 27, 1997

Related U.S. Application Data

[63] Continuation of application No. 08/331,567, filed as application No. PCT/SE93/00383, Apr. 30, 1993, abandoned.

[30] Foreign Application Priority Data

Apr. 30, 1992 [SE] Sweden .................................. 9201413

[51] Int. Cl.$^6$ .................................................. A61M 37/00
[52] U.S. Cl. .................................................................. 604/4
[58] Field of Search ...................... 604/4, 5, 6; 424/101, 424/533, 902; 435/2

[56] References Cited

U.S. PATENT DOCUMENTS

| | | | |
|---|---|---|---|
| 4,329,986 | 5/1982 | Babb | 604/4 |
| 4,500,309 | 2/1985 | Diederich et al. | 604/5 |
| 4,680,177 | 7/1987 | Gray et al. | 424/101 |
| 4,769,318 | 9/1988 | Hamasaki et al. | |
| 5,240,601 | 8/1993 | Mazio | 604/6 |
| 5,250,303 | 10/1993 | Meryman et al. | 424/533 |
| 5,288,605 | 2/1994 | Lin et al. | 435/902 |

FOREIGN PATENT DOCUMENTS

85/02116  5/1985  WIPO.

OTHER PUBLICATIONS

Transfusion, vol. 32, No. 2, 1992, F. Bertolini, et al., "Role of acetate during platelet storage in a synthetic medium", pp. 152–156.

*Primary Examiner*—Michael J. Milano
*Attorney, Agent, or Firm*—Merchant, Gould, Smith, Edell, Welter & Schmidt, P.A.

[57] ABSTRACT

The invention relates to a water-based preparation to be mixed with blood, containing citrate ions which inhibit coagulation, as well as a method applied at collection of blood from a living organism while adding an anticoagulant substance including citrate ions. The new features of the invention are that acetate, being a physiologic energy source, inter alia for platelets, is included in the preparation and is added to the blood during collection in addition to the anticoagulant substance in order to obtain prolonged shelf-life of the platelet concentrate without increased risk for the donor or patient.

28 Claims, 1 Drawing Sheet

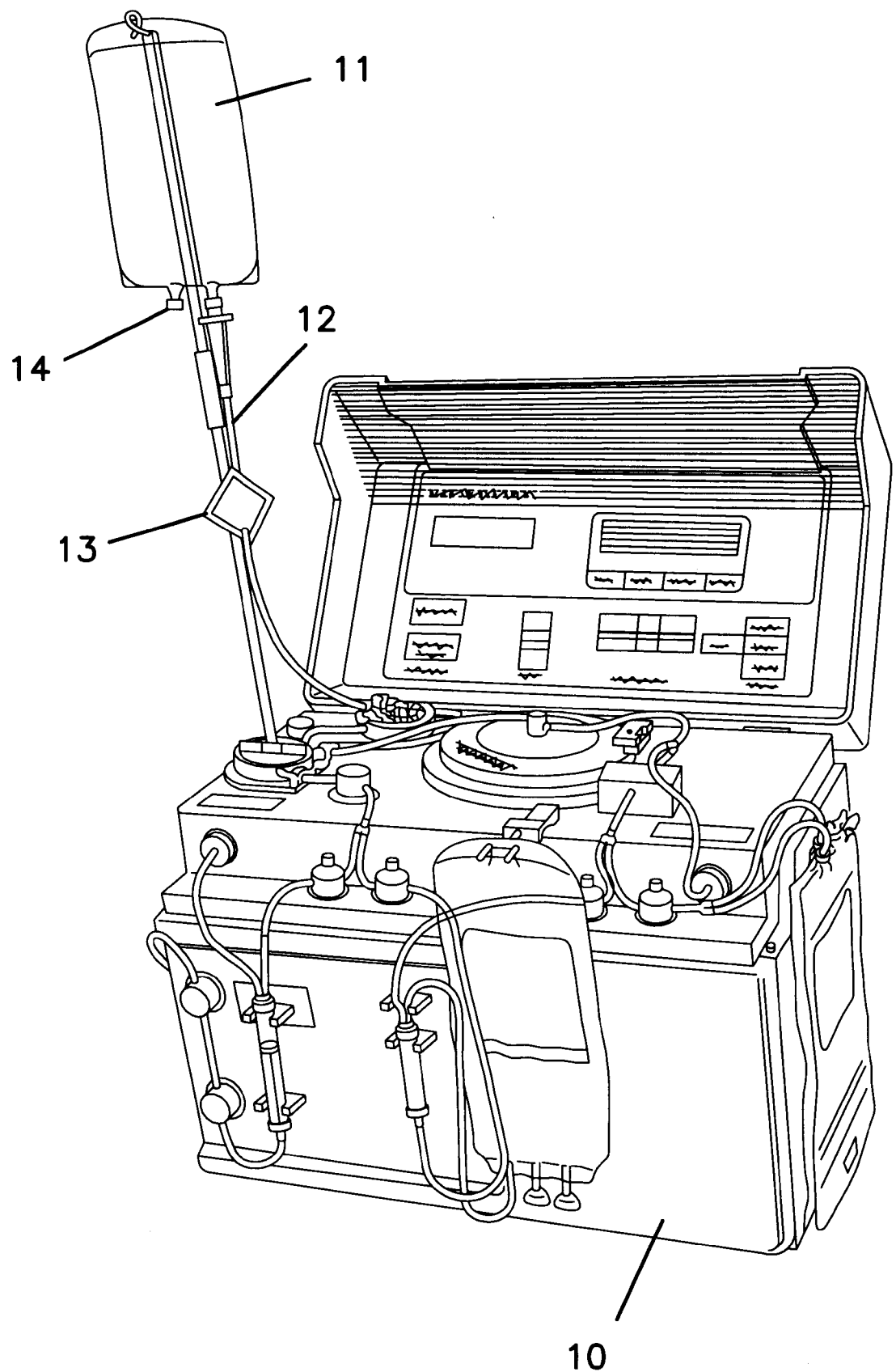

PREPARATION AND METHOD FOR PRODUCTION OF PLATELET CONCENTRATES WITH SIGNIFICANTLY PROLONGED VIABILTY DURING STORAGE

This is a Continuation of application Ser. No. 08/331,567, filed Jan. 13, 1995, now abandoned which is a 371 of PCT/SE93/00383.

BACKGROUND OF THE INVENTION

Platelet transfusion is an often life-saving form of patient treatment, since platelets are required for normal hemostasis, i.e for bleedings from wounds to stop normally; on the other hand, platelets may appear in too small numbers due to certain diseases and/or treatments. Blood donors may be the source of platelet concentrates for transfusion in two principally different ways, one being conventional whole blood donation and the other being so called platelet apheresis by means of a blood cell separator.

With the objective to make the best possible use of the unique raw material, in modern transfusion medicine it is the routine worldwide that whole blood is separated into its main components, usually according to one of the systems first described by Professor Claes Hömaan, M.D., Uppsala, Sweden. In these procedures platelets may be recovered either from the platelet rich plasma resulting from a first step of centrifugation, carried out at relatively few revolutions per minute, or from the so called buffy coat, which constitutes the top layer of blood particles after normal, harder centrifugation of the primary blood bag, in which case the supernatant plasma turns out to be virtually platelet-free.

Especially in Italy and in Sweden, a new important routine method has rapidly been established in order to satisfy the extremely great need for platelets in some hospitals, viz. so called pooling of 1–6 buffy coat preparations, including a small amount of accompanying erythrocytes and also a small volume of plasma, with the ensuing dilution with 250–300 ml of either standard saline solution or of a more complex solution containing carbohydrates and saline, followed by a final step of centrifugation low rotary speed for the elimination of erythrocytes and leukocytes from the platelet preparation.

Platelet apheresis is a procedure within transfusion medicine/blood banking, which has been well established for 10–15 years and which by use of a blood call separator makes it possible for one single donor in 60 to 90 minutes to put a full transfusion dosis of hemostatically active platelets to the disposition of a patient in need. This method of procurement has several advantages for the patient as compared with preparing a so to say pooled platelet concentrate from 4–8 whole blood units from conventional blood donation. Carried out professionally by means of blood cell separators of various kinds, platelet apheresis and similar, more frequently occurring plasmapheresis as plasma donation, are completely safe ventures.

However, platelet apheresis is an expensive procedure, particularly since the shelf-life of platelet concentrates—best stored at 20–24° C. while mixed by rocking horizontally or rotation end over end at slow speed in special plastic bags permeable to oxygen and carbon dioxide—at present is approximately 5, at the most 7 days. The high costs are also caused by the fact that the often strongly variable demands, combined with the requirements for an adequate stock-pile of platelets for emergencies, provoke a great degree of loss from outdating (e.g. in Malmö, Sweden, at a yearly cost of approximately SEK 200,000).

It has recently been demonstrated that the shelf-life of platelet concentrates may be virtually doubled by one single stroke, carried out as the (next to) last step during the preparation of pooled buffy coat concentrates by including acetate into the diluting platelet additive solution, in other words, acetic acid as the salt thereof, neutral or slightly alkaline sodium acetate. Apparently, added acetate can be used as a physiological source of energy in the so called tricarboxylic acid cycle of platelets. This system for the conversion of energy, also called Kreb's Cycle after its discoverer, is found in all living cells.

However, at variance with most other cells (stored), platelets lack the enzyme system, which can transform glucose to acetate for introduction into the tricarboxylic acid cycle. Still, glucose is metabolized in a limited way, so called glycolysis the result of which is lactic acid, causing the pH of standard platelet concentrates from apheresis or whole blood to fall with a speed related, inter alia, to platelet number and concentration of bicarbonate. The latter is the most important buffer of plasma. Typically, within 6–8 days the pH of standard platelet concentrates have fallen to below 6.5 or below 6.2, where platelets rapidly loose hemostatic capacity and viability. As pointed out by F. Bertolino, S. Murphy, R. Rebulla and G. Sirchia (Transfusion 1992; 32: 152–156) acetate per se has no buffering capacity but when available to platelets during storage it has a pH-stabilizing affect, apparently because acetate is metabolized in the tricarboxylic acid cycle as acetic acid, oxidized all the way to carbon dioxide and water. In this way, acetate is consumed together with a proton, in other words an acidifying hydrogen ion. It may be derived either from carbonic acid, thus converted to buffering bicarbonate, or directly from lactic acid being converted to virtually nontoxic sodium lactate, the overall affect being that pH may stay approximately at pH 7 for more than 12 days, as reported by these authors and coinciding with our experience at the Blood Transfusion Centre of Malmö, Sweden. It has been stressed, inter alia by S. Holme (Blood Cells 1992; 18:421–430) that maintenance of the pH of platelet concentrates at approximately pH 7 is the singular most important in vitro characteristic of viable, hemostatically active stored platelets. In fact, apheresis platelets stored in citrate (ACD-A) plasma with acetate have proven repeatedly to normalize prolonged Ivy bleeding time 12 days after donation.

From the extensive use of acetate in intravenously applied preparations for fluid substitution and from the inclusion of significant amounts of acetic acid in everyday food it is apparent that (sodium) acetate is a completely nontoxic substance as long as it is not administered so as to produce clearly nonphysiological concentrations, e.g. as in acetate-based hemodialysis, or causing osmotic side effects and the like.

In fact, intravenous drip solutions containing 50 millimoles acetate (in addition to 100 millimoles chloride and 150 millimoles sodium ion, all this per litre), particularly when given intravenously in volumes of several litres, have physiological advantages over so called physiological saline solution in that the acid-base balance of the body is not tipped to the acid side (as shown by Professor Gösta Rooth of Lund, nowadays in Uppsala).

Platelet concentrates, after being prepared by apheresis or in any other way, may then be manipulated for the addition of acetate or other substances, the condition being that it can be done without contamination of the product, especially considering the risk of bacterial growth at the actual storage temperature, 20–24° C. Also if that problem apparently can be solved today by application of expensive equipment for so called "mirror welding" of PVC tubing end to end (Haemonetics/Dupont Sterile Connecting Device SCD 312), or by preattachnent to the disposable kit of tubings, bags etc. for platelet apheresis there is the disadvantage of (concomitant) dilution of the plasma of platelet concentrates, which in turn appears to reduce the shelf-life of platelets.

SUMMARY OF THE INVENTION

The invention provides a solution to the above problem quite contrary to established principles in blood banking in as much as the solution implies that the donor of platelets produced by apheresis comes into contact with a substance novel in this context, viz. acetate. Surprising to just about everybody within blood banking and the speciality of transfusion medicine, acetate is actually an atoxic substance present all through the body and its cells. Thus, intravenous administration of reasonably limited amounts of acetate to volunteer blood donors and patients, respectively, appears as an insignificant side phenomenon of platelet donation and of platelet transfusion.

From the above statement also follows the surprise that acetate—although it is an established principle not to mix transfusion blood with anything but so called physiological saline solution—can be added to donor blood also in the context of whole blood donation by being a constituent of the anticoagulant solution, with which the donor blood is mixed and the most important constituent of which is citrate.

The invention thus relates to a water-based preparation according to claim 1, which may be manufactured industrially to be distributed to blood donation centers in order to be used there as an additive during platelet apheresis (or whole blood donation).

However, the invention also concerns a method for the collection of blood from a living individual according to claim 2, and in this method acetate may either be mixed with the anticoagulant substance or be added to the blood in parallel to this substance.

BRIEF DESCRIPTION OF THE DRAWING

FIG. 1 is a schematic drawing of the blood cell separator including a bag of anticoagulant solution.

DETAILED DESCRIPTION OF THE INVENTION

The decisive advantage of the invention is that to the platelets to be collected acetate is supplied in the supremely easiest way, either in connection with platelet apheresis or in whole blood collection, and that according to the invention this can be effected without the need for a new manipulation, new device or new procedure to be introduced as a new routine in blood donation.

The realization of the invention is surprisingly simple in that it may be achieved in parallel with the pump-controlled admixture of citrate to donor blood in volume quotients from 1:6 to 1:16, which is necessary for the blood to remain fluid and thus not to coagulate during the sensitive procedure within the blood cell separator and also to protect platelets from being activated. The solution Acid Citrate Dexrose A (ACD-A) contains sodium citrate, citric acid and dextrose= glucose and, also according to the manufacturer, has a pH of approximately 5. Therefore, direct intravenous administration to a patient or donor is explicitly forbidden, since it involves risks and no medical motivation. However, a considerable volume of plasma admixed with ACD-A is returned to a platelet apheresis donor without other side-effects than intermittent sensation of occasional drops of the concentration of calcium ions in the blood. The use of ACD-A, inter alia, during platelet apheresis is based on the knowledge that the substances involved are physiologically present in donors and that they are rapidly metabolized. Nevertheless, citrate administration almost invariably causes some limited discomfort related to the complex formation of calcium ion with citrate, a prerequisite for its function during apheresis, potentially with risks of muscle cramps and cardiac malfunction all the way to heart arrest.

By comparison, addition of sodium acetate—which may occur in a simple way through an injection port of the plastic bag containing the ACD-A solution—involves no risk whatsoever for negative effects on the part of the donor as long as the final concentration in plasma from the blood cell separator, partially retransfused and partly included in the platelet concentrate does not exceed 50 millimoles acetate per litre, optimum being half thereof or maybe just 10 millimoles per litre. When ACD-A is mixed with blood in blood separators at volume quotients from 1:6 to 1:12, such levels are obtained in the machine plasma with 3–30 millilitres 2.5 molar sodium acetate added to 500 millilitres ACD-A in a standard bag.

Another advantage of the invention is that it eliminates the increased risk for bacterial contamination through manipulation, otherwise necessary after apheresis. The contamination with air-borne bacteria, which is theoretically possible when attaching the ACD-A bag to the spike of the tubing leading to the anticoagulant pump is counteracted by the so called bacteria filter, which is integrated into this tubing, and which FDA in USA has accepted as a prerequisite allowing for up to five days storage of platelet concentrates before transfusion. Therefore, using standard needles and a syringe, also the addition of acetate to the ACD-A through the injection port for additives can be carried out without increased risk for bacterial contamination of the platelet concentrate in the other end of the system far beyond the bacteria filter. As an alternative and as a simplification acetate is added already during manufacture and thus is present during sterilization by autoclaving along with the other constituents of the bag or bottle. Another advantage of the invention is that in this manner unnecessary dilution of the plasma of the platelet concentrate will be avoided, which according to our experience may reduce the shelf-life of stored platelets.

The accompanying drawing discloses a blood cell separator 10 with a bag 11 containing ACD-A. This bag is attached to the pump for ACD-A of the separator by means of the tubing 12, including a bacteria-tight filter 13. At a connector (injection port) 14 acetate as introduced via the ACD-A bag.

In the same way, with needle acetate may be aseptically transferred to such bags, in which whole blood from blood donors is collected to be mixed therein with the anticoagulant containing citrate or heparin or, alternatively—much better—to be integrated with the manufacturing process including sterilization of the bag with its contents. Considering the fact that acetate within wide limits is atoxic and in the amounts applied cannot influence storage or use of any blood component in a negative way, it may be suitable to offer bags for whole blood donation containing anticoagulant to which acetate has been added in at least two different amounts, on one hand corresponding to what is know to be optimal for platelet production via intermediate platelet rich plasma, and on the other in 3–10 times greater amount to to allow for optimal final concentration after the dilution with saline or the like, included in the methods for the preparation of platelet concentrates from pooled buffy coats.

I claim:

1. A method for recovering a platelet concentrate from blood, the method comprising the steps of:
    obtaining blood from a donor;
    adding acetate to the blood immediately before, immediately after, or simultaneously with addition to the blood of a citrate-based anticoagulant solution; wherein the adding and addition produce treated blood; and
    separating a platelet concentrate from the treated blood.

2. The method of claim 1, wherein the platelet concentrate is platelet rich plasma.

3. The method of claim 2, further comprising the step of:
    processing the platelet rich plasma to obtain a more concentrated platelet preparation.

4. The method of claim 1, wherein:
    the step of obtaining comprises:
        connecting said donor to an apheresis machine; and
        collecting whole blood from the donor using the apheresis machine; and the step of separating comprises:
        removing platelets from the treated blood mixed using the apheresis machine;
        replacing a fraction of the treated blood back into the donor after removing platelets; and
        disconnecting the donor from the apheresis machine.

5. The method of claim 1, wherein the citrate-based anticoagulant solution is suitable for mixing with blood before blood is separated into components and suitable for supply to the donor with blood or a blood fraction returned to the donor.

6. The method of claim 1, wherein citrate is at a concentration sufficient to inhibit coagulation to an extent that coagulation does not interfere with separation of blood components.

7. The method of claim 1, wherein the citrate-based anticoagulant solution is ACD-A.

8. The method of claim 1, wherein the citrate-based anticoagulant solution is ACD-A.

9. The method of claim 1, wherein a volume of acetate and citrate-based anticoagulant solution is added to blood in a ratio of no more than about 1 volume acetate and citrate-based anticoagulant solution per about 6 volumes blood.

10. The method of claim 1, wherein the ratio is in the range of about 1 volume acetate and citrate based anticoagulant solution per about 6 volumes blood to about 1 volume acetate and citrate-based anticoagulant solution per about 16 volumes blood.

11. The method of claim 1, wherein acetate is added to a concentration of less than or equal to about 50 mM.

12. The method of claim 11, wherein acetate is added to a concentration of about 25 mm.

13. The method of claim 11, wherein acetate is added to a final concentration of about 15 mM.

14. The method of claim 1, further comprising the step of preserving platelets for at least 7 days.

15. The method of claim 14, wherein platelets are preserved for 7 days to about 12 days.

16. An acetate containing anticoagulant composition consisting essentially of:
    a citrate-based anticoagulant solution comprising a concentration of citrate sufficient to inhibit coagulation to an extent that coagulation does not interfere with separation of blood components;
    acetate ion; and
    a counterion.

17. The composition of claim 16, wherein the citrate-based anticoagulant solution is suitable for mixing with blood before blood is separated into components and suitable for supply to the donor with blood or a blood fraction returned to the donor.

18. The composition of claim 16, wherein the citrate-based anticoagulant solution is ACD-A.

19. The composition of claim 16, wherein the citrate-based anticoagulant solution is ACD-A.

20. The composition of claim 16, wherein the composition is effective to preserve platelets and inhibit coagulation when added to blood in a ratio of no more than about 1 volume composition per about 6 volumes blood.

21. The composition of claim 20, wherein the composition is added to blood in a ratio of about 1 volume composition per about 6 volumes blood to about 1 volume composition per about 16 volumes blood.

22. The composition of claim 16, wherein the composition comprises a concentration of acetate less than or equal to about 50 mM.

23. The composition of claim 22, wherein the composition comprises about 25 mM acetate.

24. An acetate containing anticoagulant composition comprising the citrate-based anticoagulant solution ACD-A and acetate ion.

25. The composition of claim 24, wherein the composition is effective to preserve platelets and inhibit coagulation when added to blood in a ratio of no more than about 1 volume composition per about 6 volumes blood.

26. The composition of claim 25, wherein the composition is added to blood in a ratio of about 1 volume composition per about 6 volumes blood to about 1 volume composition per about 16 volumes blood.

27. The composition of claim 24, wherein the composition is effective to preserve platelets for at least 7 days.

28. The composition of claim 27, wherein the composition preserves platelets for 7 days to about 12 days.

* * * * *